United States Patent [19]

Shaw

[11] 4,224,303
[45] Sep. 23, 1980

[54] SIGNALLING PARTICLES FOR INTRODUCTION INTO BLOOD FLOWING THROUGH A VESSEL OF INTEREST

[75] Inventor: Robert F. Shaw, Portola Valley, Calif.

[73] Assignee: A. C. Smith

[21] Appl. No.: 926,841

[22] Filed: Jul. 21, 1978

Related U.S. Application Data

[60] Division of Ser. No. 487,425, Jul. 10, 1974, Pat. No. 4,111,191, which is a continuation of Ser. No. 249,161, May 1, 1972, abandoned.

[51] Int. Cl.² ............... A61K 29/00; A61K 43/00
[52] U.S. Cl. ...................................... 424/1; 128/1.2; 424/1.5; 424/9
[58] Field of Search ............ 424/1, 9, 1.5; 128/2 A

[56] References Cited

U.S. PATENT DOCUMENTS

| | | | |
|---|---|---|---|
| 3,812,245 | 5/1974 | Dugan | 424/1 |
| 3,933,996 | 1/1976 | Charlton et al. | 424/1 |
| 3,995,020 | 11/1976 | Dandamudi | 424/1.5 |
| 4,126,669 | 11/1978 | Rothman et al. | 424/1 |

*Primary Examiner*—Benjamin R. Padgett
*Assistant Examiner*—Christine M. Nucker
*Attorney, Agent, or Firm*—A. C. Smith

[57] ABSTRACT

Particulate sources of signal which can be detected outside the body of a patient are introduced into the circulating blood and are tracked in three dimensions in the region of the heart using suitable detectors disposed about the patient's chest. This permits the sequence of positions of each particle to be recorded as a function of time as each particle flows through a coronary vessel. Data analyses of these recordings of particle positions provide information about the velocity of blood flow through the course of each coronary artery. This velocity information is used to determine the extent, severity and location of stenotic lesions of the coronary arteries.

6 Claims, 6 Drawing Figures

SIGNALLING PARTICLES FOR INTRODUCTION INTO BLOOD FLOWING THROUGH A VESSEL OF INTEREST

CROSS REFERENCE TO RELATED APPLICATION

This is a divisional application of pending application Ser. No. 487,425 filed July 10, 1974, now U.S. Pat. No. 4,111,191, which is a continuation application of application Ser. No. 249,161 filed May 1, 1972, now abandoned.

BACKGROUND OF THE INVENTION

Coronary heart disease (CHD) is the leading cause of death in the United States and the western world. Coronary heart disease accounts for almost two-thirds of male deaths during that period of life (30–64 years) when responsibilities to family and society are the greatest. Approximately one-third of individuals dying of coronary heart disease succumb immediately after coronary occlusions; one-third die within a few hours; and only one-third receive the benefits of hospital therapy. Of all individuals sustaining their first myocardial infarction, more than half have had neither preceding signs nor symptoms of coronary heart disease.

During the past two years, coronary vein-graft bypass surgery has been demonstrated to be an effective therapeutic modality of wide applicability. Because over 70% of all coronary artery stenoses occur in the first 4 cm. of the coronary arterial tree, a high percentage of all coronary lesions can be surgically by-passed with a low mortality and high patency rate.

Extensive epidemiological studies have delineated those factors (hypercholesterolemia, hypertension, obesity, and heavy smoking) that are statistically correlated with an increased incidence of coronary heart disease. But while a patient may be well advised to remove himself from the higher risk group by appropriately altering his manner of living, these indices cannot for any given patient furnish information concerning the existence of coronary stenotic lesions nor furnish a basis for clinical decisions regarding therapeutic intervention.

Electrocardiograhic stress testing has been suggested as a means for screening individuals for significant coronary lesions. However, in a large prospective study in which subjects underwent repeated testing, the sensitivity of this test was found to be too low (only 30%) to be adequate.

At present, coronary arteriography yields more useful information about the state of the coronary arteries than any other technique. However, in a large cooperative study, the incidence of major complications was 2% and the mortality rate was 0.23%. In addition to the dangers, the procedure is painful, expensive, and time-consuming. For these reasons, coronary angiography is not performed upon asymptomatic individuals and is not suitable for screening large populations.

The above considerations highlight the importance of the subject invention which furnishes the capability for detecting the extent, location and severity of coronary stenotic lesions by means of apparatus operating external to the body, thereby identifying, by means suitable for screening large populations, candidates for remedial coronary surgery and other therapeutic measures.

SUMMARY OF THE INVENTION

In accordance with the present invention, stenotic atherosclerotic lesions of the coronary arteries are detected by injecting a number of positron-emitting particles into the circulating blood of a subject to determine the velocity of blood flow through his coronary vessels.

Because of the high peripheral resistance of the myocardial vascular bed and the considerable range of autoregulatory resistance changes available to the coronary circulation, coronary stenoses of 80%–90% are required to diminish the volume of coronary blood flow. This propensity of volumetric coronary blood flow to remain normal even in the presence of severe stenoses is responsible for the late occurrence or absence of anginal symptoms and diagnostic electrocardiogram patterns, even in the presence of coronary stenoses, and explains why measurement of volumetric blood flow furnishes poor sensitivity in detecting coronary disease.

However, this propensity of volumetric blood flow to remain normal even in the presence of severe stenosis furnishes a distinctive characteristic that blood flowing through a stenotic arterial segment must have high velocity. In fact, to maintain the constant volumetric flow rate, the average fluid velocity within a stenotic segment of artery must change in strict inverse proportionality to the change in cross-sectional areas from normal to stenotic blood vessel. As coronary stenosis becomes more severe, the increments in blood flow velocity become progressively greater.

Discrete positron-emitting radioactive particles of sufficiently small size to pass through capillary beds are injected intravenously and become randomly distributed in the circulating blood volume. The particles are tracked in three dimensions whenever they appear in the region of the heart by means of high resolution high-speed gamma detectors that surround the chest. These recordings of particle position as a function of time are analyzed and whenever a particle follows a flow path indicating that it is passing through a coronary artery, the velocity of blood as it flows through the artery is measured by timing the transit of the particle. From the accumulated data of multiple particle transits through the coronary circulation, a three-dimensional representation of the lumen of the coronary arterial system is constructed.

DESCRIPTION OF THE PREFERRED EMBODIMENT

Figure 1:
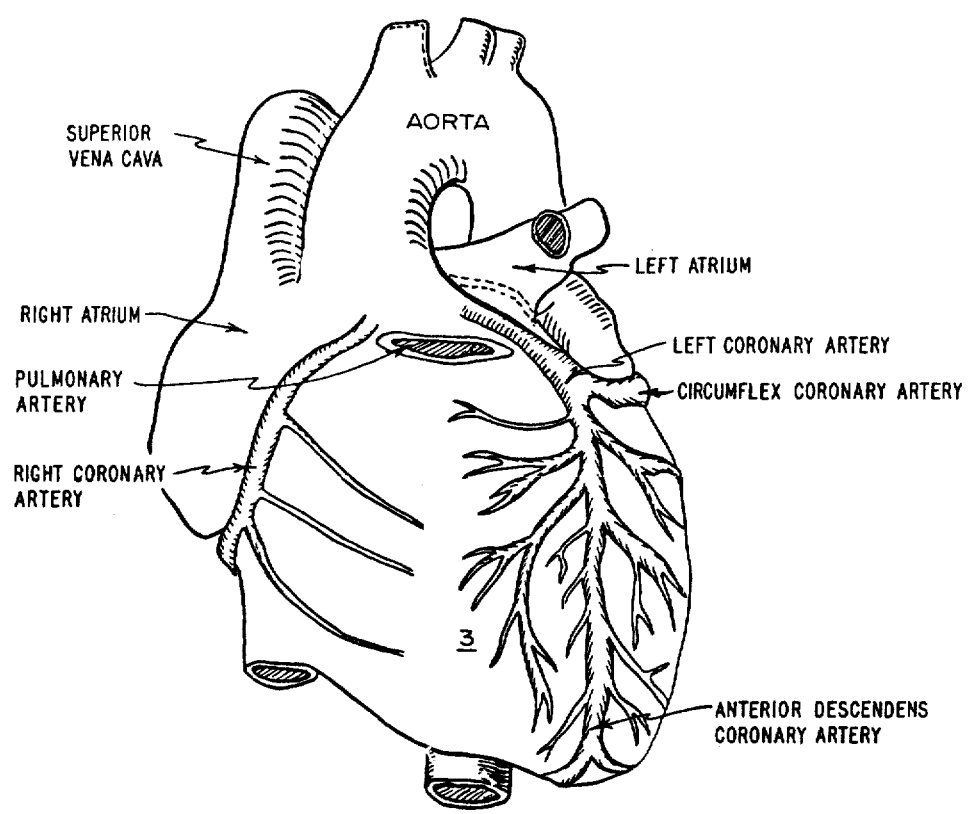
FIG. 1 is a pictorial view of a human heart showing the principal coronary arteries.

The main coronary arteries are three in number. These three vessels branch somewhat irregularly to form an average of ten secondary vessels, as shown in FIG. 1. Arteriosclerotic lesions are limited to the epicardial segments of the coronary vessels and rarely extend beyond the most proximal portions of the secondary vessels. The highest concentration of arteriosclerotic lesions is within the first 2 to 3 cm. of the left anterior descendens artery 3, but the lesions are otherwise rather randomly distributed in the proximal primary and secondary arteries. Seventy percent of all arteriosclerotic coronary lesions are found within the proximal 4 cm. of the main coronary arteries.

The average velocity of blood flow through the epicardial coronary blood vessels is of the order of 30 cm/sec. A 50% stenosis is generally considered to be significant. To be useful, the system should be capable of discriminating between normal vessels and 50% stenotic lesions and should be capable of assessing additional significant decrements in the patent cross sections of these vessels.

Typical blood flow velocities through stenoses of varying degrees are as follows:

| Degree of Stenosis | Average Velocity |
| --- | --- |
| 0% | 30 cm/sec |
| 50% | 60 cm/sec |
| 60% | 75 cm/sec |
| 70% | 100 cm/sec |
| 80% | 150 cm/sec |
| 90% | 300 cm/sec |

Since nominal resting coronary flow velocity is about 30 cm/sec, ideally the system should be able to differentiate a flow velocity of 60–75 cm/sec from 30 cm/sec in order to detect significant lesions and discriminate between velocities of 75, 100, 150, and 300 cm/sec in order to follow additional 10% increments in stenoses.

For a number of years, positron-emitting isotopes have been used to carry out tracer studies. A positron from a typical emitting radionuclide will travel some millimeters in blood or tissue before coming to rest. It will then be captured by an electron in the local tissue and both particles will be annihilated producing two gamma rays, each of 511 KeV moving in almost exactly opposite directions. If both gamma rays can be detected at some distance with good spatial resolution, then a straight line joining the points at which the gamma rays were detected must pass through their mutal point of origin and within a few millimeters of the positron-emitting source. If a number of gamma pairs are detected from a single stationary source and several (in principle, two) such lines are drawn, the lines will intersect at one point in space and define the position of the positron-emitting source.

In the conventional applications of positron technology which have been made to date, rather poor resolution has been all that was required. A radioactive tracer is injected and then concentrates to some extent in an organ of interest. Typically, conventional detectors have spatial resolutions of the order of a centimeter. Since the organ being examined is normally stationary, any additional resolution is obtained by observing a statistically large number of counts.

In accordance with the preferred embodiment, the present invention tracks a number of discrete moving positron-emitting sources present in the circulating blood. The system not only locates the position of the sources in three dimensions, but also locates them again and again at very short time intervals. The requirement as to how often a particle source must be located is determined from the following considerations.

As noted above, 30 cm/sec is about the nominal velocity of blood flow through a coronary artery for a subject at rest. Blood flow through a diseased arterial segment which is 80% stenotic will have a velocity five times this nominal value (150 cm/sec). Blood flowing through a segment of a blood vessel with a severe 90% stenosis will have a velocity of the order of 300 cm/sec. In order to measure a 90% stenosis that is 1 cm long, a particle moving through the stenosis should be detected at least a few times. At 300 cm/sec, only three milliseconds are required to pass through a 1 cm length of vessel. If three determinations of position are desirable during this interval, a half-dozen coincident pairs of gamma rays must be detected during the three milliseconds and a minimum detection rate of 2,000 gamma pairs per second is indicated.

The detector of the present invention subtends about two-thirds of the total solid angle surrounding the heart. Each gamma ray has a 50% probability of leaving the body undeflected. There is thus a $(0.5)^2 = 0.25$ probability that both members of a gamma pair will emerge from the body undeflected.

If the detecting element has a 20% efficiency for detecting a gamma ray incident upon it, then there is a $(0.20)^2 = 0.04$ probability of detecting both members of a coincident pair. Multiplying these numbers together furnishes the over-all probability that a positron annihilation will produce a detected pair of $$P = 0.67 \times 0.25 \times 0.04 = 0.0067$$

Thus, it takes 150 annihilations on the average to produce one detected pair. For 2,000 detected gamma pairs per second, each source must emit $2{,}000 \times 150 = 3 \times 10^5$ positrons per second. $3.7 \times 10^5$ positrons per second correspond to a 10 microcurie source, so individual source intensities on the order of 10 microcuries are indicated.

Sources of this or many times greater intensity are routinely available, but the particles used in this application must be sufficiently small to pass through capillary beds, if they are to be injected by simple venipunctures and find their way to the coronary arteries. Fortunately, there exist a considerable number of positron emitters (such as $Gallium_{68}$) which have half-lives of sufficiently short duration so that a small number of atoms produce a high decay rate. For example, $Gallium_{68}$ has a half-life of only 68 minutes and can be readily, conveniently, and inexpensively "milked" from $Germanium_{68}$, an isotope with about 270 days half-life. A pure Gallium source of one cubic micron volume has an intensity of 230 microcuries. While pure $Gallium_{68}$ is unsuitable because it is a liquid at body temperature, the large carrier-to-active material ratios for particles having a short dimension less than 6–8 microns suggest that $Gallium_{68}$ either compounded or absorbed in carrier particles would provide a suitable source.

As noted above, there are three main coronary arteries which branch into an average of ten secondary branches. If, for statistical purposes, it is desired that three velocity measurements be made through each of the ten secondary branches, then a total 3×10=30 particle transits through the coronary system would be required. This would furnish approximately 10 transits through each of the proximal principal coronary arteries where most of the atheromatous lesions are located.

Since coronary blood flow approximates only 5% of the cardiac output at rest, a given particle has only a 0.05 probability of entering the coronary circulation after a single pass through the heart. Thus, 20 circulations through the heart times 30 particle transits through the coronary system, or a total of 600 particle transits through the circulation would furnish the redundancy of coronary blood flow velocity measurements outlined above.

Since the mean circulation time is one minute or less, a single particle tracked in the circulation for 600 minutes would be suitable for the outlined redundancy, if its half-life were sufficiently long and if it continued to circulate for the ten-hour period. Of course, ten hours is an inconveniently long duration for a diagnostic measurement. Forty particles circulating for fifteen minutes would be much more convenient and would furnish a comparable 600 particle transit through the circulatory system.

The number of particles required to attain 600 particle transits through the circulation is influenced by the possibility that the positron-emitting particles may be removed from the circulation by the Kupfer cells of the liver. The propensity of the liver to extract particles is a function of their size and surface characteristics, of the state of the reticulo-endothelial system as influenced by pre-treatment and otherwise, and a function of other variables.

Liver blood flow is on the order of 20%–25% of cardiac output at rest. If particles are extracted by the liver with 100% efficiency, a total of 160 particles would have to be administered and the examination conducted for a fifteen-minute period in order to furnish the desired 600 circulatory transits under these circumstances. A reasonable program of particle administration might begin with an initial intravenous injection of 50 particles, with 12 particles injected at the end of each of nine subsequent 1-minute periods. Alternatively, if particles are extracted from the liver with less than 100% efficiency, the number of particles required for a fifteen-minute examination would fall between 160 and 40.

The number of particles used for an examination is important in two regards: the radiation exposure of the patient and the complexity of the data processing required. If liver extraction is 100% efficient, the total administered dose is 160 particles × 10 microcuries per particle = 1.6 millicuries, which compares favorably with the 2 millicurie Gallium$_{68}$ dose currently administered for bone scanning. Radiation to the liver for this worst case is 3 rads, which compares favorably with the liver dose of 6 rads which results from conventional liver scans using Gold$_{198}$. However, if the circulating particles are not picked up by the liver during the fifteen-minute examination time, only 40 particles constituting 0.4 millicurie need be administered. Since Gallium$_{68}$ has a radioactive halflife of only 68 minutes, if the circulating particles are not extracted by the liver over a period of a few hours, radiation of the liver is essentially zero and radiation to the rest of the body is so widely dispersed as to be negligible.

The complexity of data processing is significantly influenced by the number of particles that must be simultaneously detected in the field of view which encompasses the heart. The coincidence circuit 9 and gates 11, 13, shown in FIG. 2, connected to the gamma detectors 7, 8 of the type shown in FIG. 3, constitute a preprocessing circuit that accepts only those gamma rays which occur as synchronous pairs and which emerge from the general region of the heart. The field of view of detectors 7 and 8 thus situated contains only 5%–7% of the total blood volume. Even if the efficiency of hepatic extraction is 100%, the total number of particles in the entire circulating blood volume at any one time need be no more than 50 to obtain the highly redundant number of measurements described above. Under these extreme circumstances, no more than 3–4 particles need be in the field of view at any one time, a very acceptable number for uncomplicated data processing.

Figure 2:
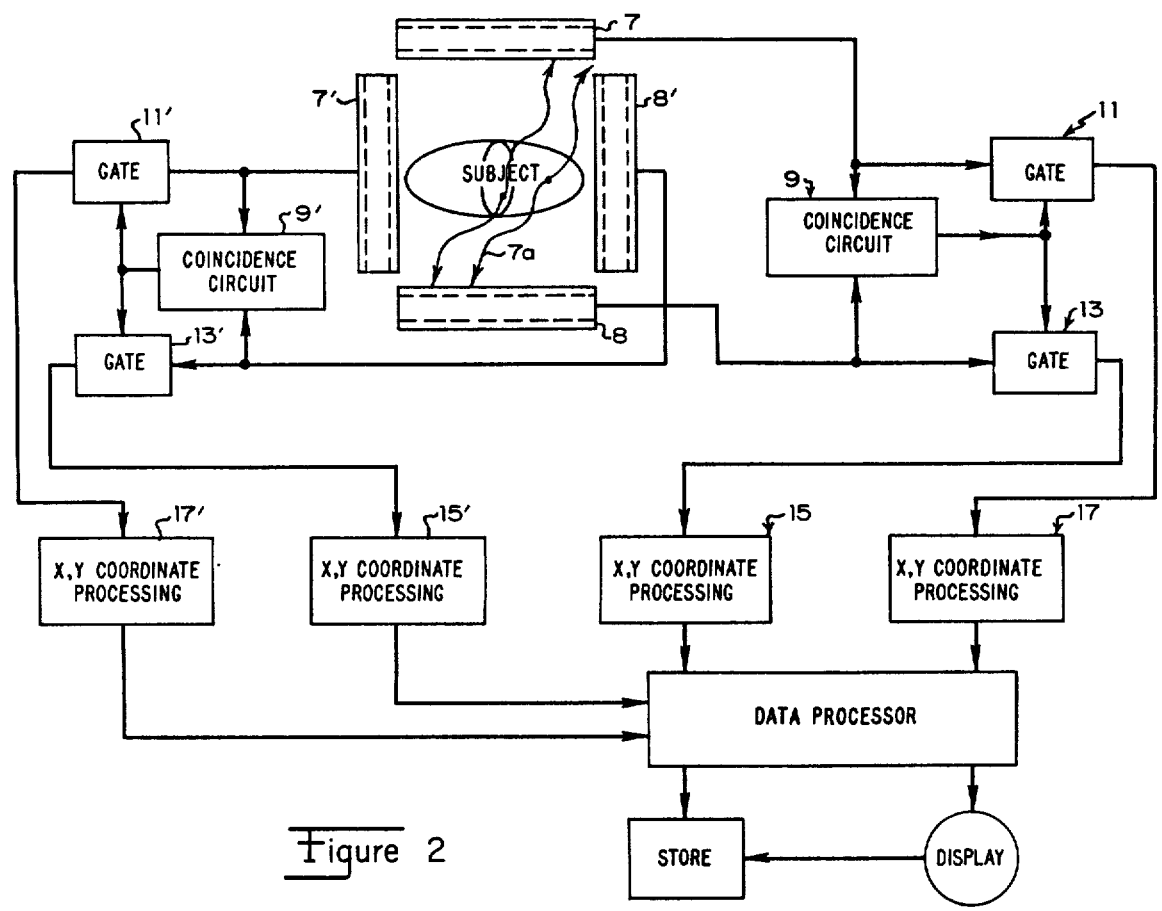
FIG. 2 is a schematic diagram of the apparatus of the present invention showing the radiation detectors disposed about the region of the heart of a subject.
Figure 3:
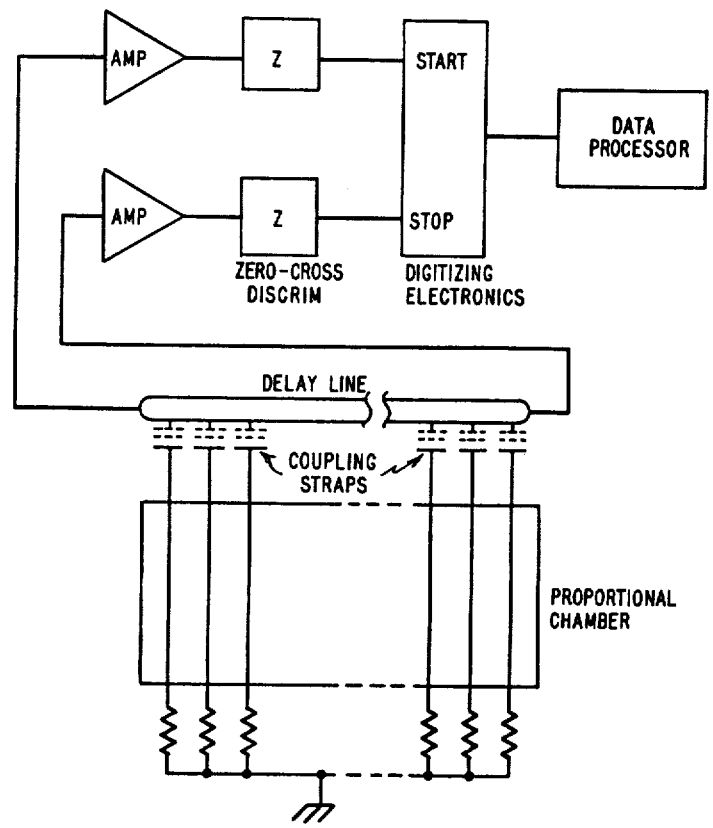
FIG. 3 is a schematic diagram of a conventional multiwire proportional chamber which may be used as the detectors in the apparatus of FIG. 2.

The detectors 7 and 8 consist of two or more pairs of detecting modules, for example, of the type shown in FIG. 3, which surround the thorax, as shown in FIG. 2, and locate the arriving gamma rays to an accuracy of about a millimeter. This information, which exists in the form of electrical pulses, is stored, say on tape or disc, depending on the rate of events, for subsequent computer processing. As noted, only gamma rays that arrive synchronously on opposing detectors 7 and 8 in FIG. 2 and only synchronous pairs that could have originated in the region of the heart are accepted for recording. Thus, gamma rays 7a that arrive synchronously from a region beyond the heart may be conveniently rejected as irrelevant data.

Figure 5:
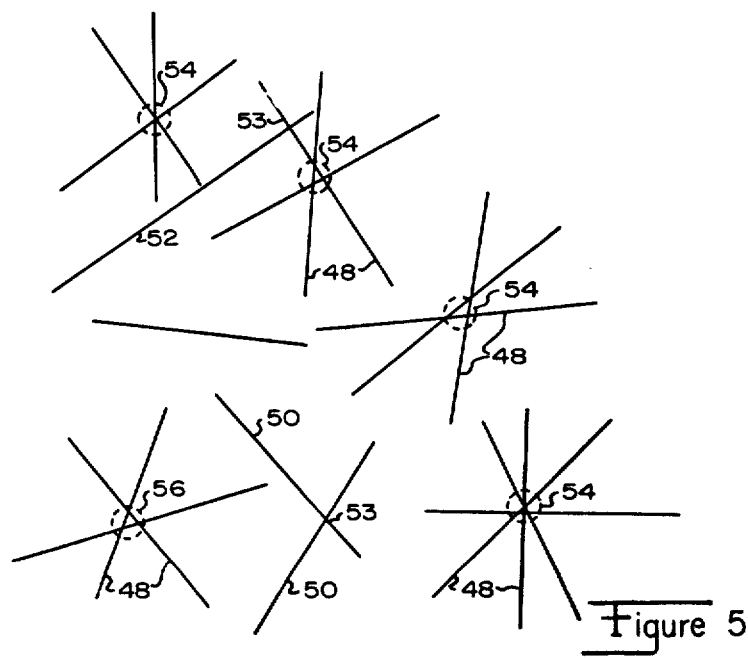
FIG. 5 is a pictorial representation of data accumulated during a single time bin of operation according to the present invention.

Subsequent computer processing of the stored data constructs straight lines in space corresponding to the inferred flight paths of the recorded gamma rays as represented in the pictorial presentation of FIG. 5. Three times out of four, at least one of the gamma rays will have been Compton scattered, producing a line 50 which does not pass through the point at which the gamma rays actually originated. These lines 50 are rejected in the data analysis because they do not consistently intersect other lines in the region of the same slowly-moving point in space. Intersections of the "true" lines will cluster together near one point 54 in space, corresponding to location of a source at a given time, which moves with a velocity of a few tens or hundreds of cm/sec. The intersections 53 of "spurious" lines are scattered randomly about and do not converge near any point.

It is desirable to minimize this background clutter of spurious lines against which the sources must be "seen," since the "true" lines do not pass through a perfect point of intersection, but through a region of ambiguity of a few millimeters in size, smeared by the variable distances and directions in which the positrons move from the source before annihilating and by the motion of the surface of the heart, where the coronary arteries of interest are located. In accordance with the present invention, the system can be operated through synchronized gates in order to observe sources only during the diastolic phase of the cardiac cycle when heart motion is least and the velocity of blood in the coronary arteries is greatest and most constant. Cardiac diastole characteristically occupies 400–600 milliseconds, which is considerably longer than the transit time (30–300 milliseconds) required for a particle to flow through a 10 cm length of coronary artery. As a result, data may be accumulated during a single diastolic period to provide a plurality of ray-intersection "clusters," as represented pictorially in FIG. 5.

Further computer processing of the intersections of the "true" straight lines reconstructs the positions of the positron-emitting sources in three dimensions as a function of time as they passed in the circulating blood through the field of view of the pairs of detector modules 7, 8 of FIG. 2. These intersections are accumulated in a number of time bins and are reconstructed to represent the flow paths of the particles. In practice, an operator may conveniently interface with the computer during this phase of data analysis to discriminate between the flow paths which represent transit through a coronary vessel and the flow paths which represent entrance to and exit from the chambers of the heart. This type of operator discrimination is simplified by the fact that these two kinds of flow paths are quite different, both spatially and with respect to relative flow velocities during the various phases of the cardiac cycle, and by the fact that an average of only three to four particles are typically in view at any one time.

In operation, then, an event is accepted by the hard-wired electronics if a signal is received at two detector chambers within about 50 nanoseconds and if the spatial locations of the two chambers indicate the event originated in a small volume encompassing the heart. These events may be stored, for example, in a disc memory device.

Figure 6:
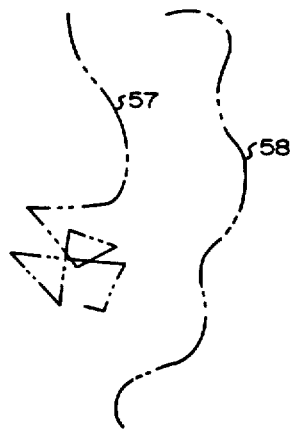
FIG. 6 is a pictorial representation of displayed data patterns representative of various particle trajectories in and about the heart of a subject.
Figure 4:
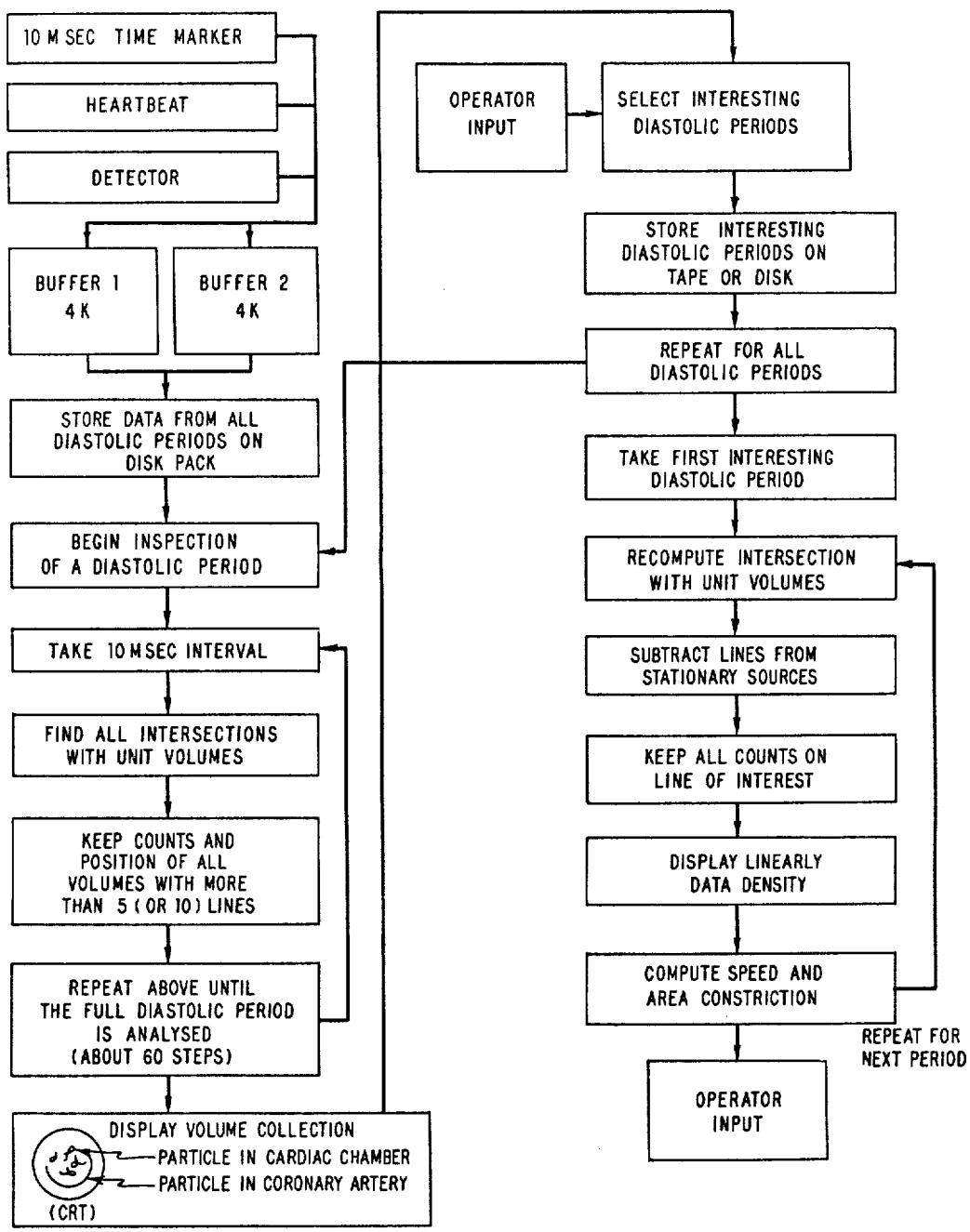
FIG. 4 is a process diagram showing operation of the data processor of FIG. 2.

The information thus stored may typically consist of 20 bits for the x, y coordinates for each side of the detector, and 4 bits for gap identification within the module, if a multiple layer multi-wire proportional chamber is used as the detector. Thus, each event (a synchronous pair of gamma rays) may require four 12-bit words to identify it. In addition, ECG information and a 10 millisecond time marker may be stored on the disc to allow for correlation between the event and the cardiac cycle. Analysis may then be performed by the following steps:

Starting with the onset of cardiac diastole, the data can be divided into 10 millisecond time bins. Each bin may be analyzed on a 10 by 10 by 10 cm$^3$ matrix where the unit volume is 1 cubic cm. Each intersection of two or more lines (corresponding to the synchronous pair of gamma rays) within a unit volume is stored as an event and only those unit volumes with more than 5 (or 10) events stored in them will be selected. On the average, not more than two to five unit volumes will satisfy this criteria for each time bin. Storage may be provided for ten of them. The counts in the unit volume selected and its position may thus be stored separately and the process will be repeated for the next 10 millisecond period. Once all intervals within a diastolic period are analyzed, the intersections representative of the positions of the particles can be displayed sequentially, as shown pictorially in FIG. 6, for all time bins during a diastolic period. Particles that were resident in the cardiac chambers during diastole exhibit characteristic lines 57 having short random segments. Particles that flowed through a coronary vessel during diastole exhibit a long line 58 of characteristic contour corresponding to the course of a coronary artery. An operator may view these data patterns which represent transits of particles in and about the heart and perform simple data selection based upon the geometry of the flow transit paths 57, 58. Data corresponding to particles which passed through a coronary artery are selected and data corresponding to particles which entered into and resided in a cardiac chamber (or took some other extra-coronary path such as through a lung) are rejected.

The data thus selected for each path of interest during a diastolic period can be redisplayed on an effectively expanded time scale in order to determined the sequential location of each particle with greater time resolution. In stenotic regions of faster blood flow, a lower number of events per unit volume will be encountered and this information about sequential locations of a particle with respect to time is used to determine the relative velocities of a particle over the total course of the flow path along the coronary artery.

This process can be repeated for all diastolic periods of the examination and, from the information thus accumulated, the existence, location, severity and extent of stenotic and dilated regions of the coronary arteries can be determined.

THE PARTICLE RADIATORS

One important constraint governing the suitability of a positron source concerns the energy of the positrons emitted. It is desirable to limit the range that the positron travels in tissue before annihilation and conversion to gamma pairs in order to minimize the sphere of confusion in inferring the radionuclide position from intersection of the lines-of-flight of gamma pairs. Since the range of 1 MeV positron is about 0.5 gm/cm$^2$ or 5 mm in tissue, it is desirable to have the mean positron energy below 1 MeV. The circulating particles should be no longer in their smallest diameter than 6-8 microns so that they will freely pass through capillary beds and each particle should produce at least $3 \times 10^5$ positrons per second. The specific activity (number of radioactive decays/second/gram) of a radionuclide required to furnish this positron rate in a particle of the small size indicated will depend upon the physiochemical properties of the radionuclide and the manner in which it forms particulates with carrier materials. The specific activity of a radionuclide is inversely proportional to its half-life. Acceptable half-lives must take into account the method of production of the radionuclide and the time required to chemically or physically convert the radionuclide into suitable particle form.

Gallium$_{68}$ is an attractive source candidate, because of its following radioactive properties:

| | |
|---|---|
| half-life | 68 minutes |
| decay product | stable $^{68}Zn$ |
| modes of decay | 88% $^+$ of which 86% goes to ground state of $^{68}Zn$ |
| mean positron energy | 1 MeV |
| production | from decay of Germanium$_{68}$, which has a half-life of 275 days |

Gallium$_{68}$ is a short-lived daughter continually produced by a long-lived parent. Germanium$_{68}$ "cows" are commercially available at low cost (less than $1,000 for the specific activity required for the worst case discussed above). The Gallium$_{68}$ produced by these generators is conveniently removed from the Germanium cow by eluting with an aqueous EDTA solution. Ga$_{68}$ can be liberated from the Ga-EDTA complex by mixing with a strongly acetic iron solution or boiling away the EDTA.

Gallium is a chemically highly reactive element which readily forms many inorganic, insoluble compounds with iron, tin, sulfates, chromates, phosphates, etc. One easily produced crystalline complex is (Ga)

$(Cr)(PO_4)_2$, formed by adding a phosphate buffered chromic salt to the eluted $Ga_{68}$-EDTA complex and boiling away the EDTA and water. The resulting crystals may be conventionally pulverized and screened to the requisite size in a diluent suitable for intravascular administration. Of course, other radiation-emitting sources may be used in accordance with the present invention. For example, particulate X-ray sources may be introduced into the blood and the direction may be performed by recurring exposures for brief intervals of photographic film positioned about the thorax of a patient.

THE DETECTOR

The detector system consists of one or more pairs of modules 7, 8, 7', 8', preferably arranged surrounding the subject's chest, as shown in FIG. 2. Each module 7, 7', 8, 8' may be a sandwich of five multi-wire proportional chambers coupled to 1 mm lead converters according to conventional design. Such modules have an active area of 50 cm × 50 cm and a total thickness of 5 cm. The 0.511 MeV annihilation photons are converted to electrons in the lead and the annihilation vectors are determined from two opposing multi-wire proportional chambers (FIG. 2). Detectors of this type, where multiplication without sparking is used to determine the position of events, are described in the literature (see, for example, Charpak, et al., Nucl. Inst. Methods 62:262, 1968; 65:217, 1968; 88:149, 1970). Detectors of this type may consist of three-wire grids with the central grid held at a positive d.c. voltage with respect to the outer two grids. For the purpose of gamma ray imaging, one of the outer grids is replaced by a lead converter which is placed very close to the high voltage grid ($\approx 1$ mm). The two grids have wires at right angles to each other and can be placed further apart (5-10 mm). The conversion electrons in passing through the gas in the chamber produce electron-ion pairs. These electrons are accelerated towards a positive high voltage wire, undergoing rapid multiplication in the high field region surrounding the wire. This results in a voltage pulse on the wire. A similar pulse is induced on the wires of the ground plane. Determining the wires on which these pulses occur gives the spatial location of the event. This may be done by capacitively coupling the wire grids to delay lines, as shown in FIG. 3. Measuring the time difference between the generation of the pulse and its arrival at the end of the delay line indicates the position of the origin of the pulse on the delay line and thus the spatial location of the event. The present technique allows spatial location accuracy of 1 mm, data rates of over $10^5$/second and resolving times of the order of 30-60 nanoseconds. Of course, the wire grids may all be coupled to a central processing unit or computer for direct determination and location of simultaneously occurring pairs of annihilation photons.

Even for pure positron-emitting sources, the majority of detected events consists of a single gamma ray, the other escaping the system because of its limited acceptance and detection efficiency. Also, some of the annihilation photons may convert in tissues surrounding the source, thus further reducing potential coincidence counts in both detectors.

Considering only the hardware-related part of this problem and including a factor of 0.25 for Compton scatter of the annihilation photons, for identical detectors 7 and 8 mounted symmetrically on four sides of a cube, as shown in FIG. 2, we may define:

G as the geometric acceptance of the system for the particular source position e as the efficiency for the detection of a single 511 KeV photon N as the number of annihilations per second occurring at the source $\tau$ as the resolving time of the chamber For the case of a pure positron emitter, we set:

$G = 0.66$
$e = 0.20$
$\tau = 50 \times 10^{-9}$ sec
$N = 10$ microcurie $Ci = 3.7 \times 10^5$ sec The rate of accidental coincidences A due to the detection of two uncorrelated events is:

$$A = G^2 e^2 N^2 \tau = 125/\text{sec}$$

which is distributed almost uniformly over the field, causing a low background data density. The number of real events R is:

$$R = 0.25 Ge^2 N = 2.5 \times 10^3/\text{sec}$$

concentrated over a small volume. The singles average data rate at each chamber is:
$S = G/2 \times e/5 \times N = 4.8 \times 10^3/\text{sec}$ which is well within the capabilities of such a detector.

I claim:

1. Particles for introduction into the blood of a subject to interact with apparatus that can detect signals outside the body of the subject, the particles having a dimension not greater than approximately 8 microns for passing through capillary beds of the body of the subject.

2. Particles as in claim 1 wherein the particles are sources of radiation.

3. Particles as in claim 2 wherein the sources of radiation produce gamma rays.

4. Particles as in claim 3 wherein the source of radiation produces gamma-ray pairs that propagate substantially in opposite directions from the region of a particle.

5. Particles as in claim 4 wherein said source emits positrons at an energy level of less than approximately 1 MeV.

6. Particles as in claim 5 wherein the source of positrons includes $Gallium_{68}$.

* * * * *